United States Patent [19]

Somers

[11] Patent Number: 5,515,866
[45] Date of Patent: May 14, 1996

[54] HARNESS FOR ABDOMINAL CATHETER SUPPORT BAND

[76] Inventor: Kenneth C. Somers, 1000 E. Walton Rd., Shepherd, Mich. 48883

[21] Appl. No.: 374,956

[22] Filed: Jan. 19, 1995

Related U.S. Application Data

[62] Division of Ser. No. 218,670, Mar. 25, 1994, Pat. No. 5,415,183.

[51] Int. Cl.⁶ ............................. A61G 15/00; A61M 5/32
[52] U.S. Cl. ............................................ 128/845; 604/179
[58] Field of Search ....................... 128/869, 875, 128/876, 877, 878, 879, DIG. 6, 845, 846; 604/179

[56] References Cited

U.S. PATENT DOCUMENTS

| | | |
|---|---|---|
| 1,310,958 | 7/1919 | O'Connor . |
| 1,828,015 | 10/1981 | Allebach . |
| 1,983,636 | 12/1934 | Palkens . |
| 2,062,586 | 12/1936 | Lawrence . |
| 2,677,488 | 5/1954 | Prvsan . |
| 3,088,438 | 5/1963 | Oliphant . |
| 4,088,136 | 5/1978 | Hasslinger ............................. 604/179 |
| 4,308,629 | 1/1982 | Freeman . |
| 4,324,205 | 4/1982 | Goldmacher . |
| 4,355,635 | 10/1982 | Bihl et al. . |
| 4,479,267 | 10/1984 | Radowsky, Jr. . |
| 4,569,348 | 2/1986 | Hasslinger ............................. 604/179 |
| 4,582,508 | 4/1986 | Pavelka ............................. 128/DIG. 6 |
| 4,666,432 | 5/1987 | McNeish ............................. 604/179 |
| 4,846,807 | 7/1989 | Safadago ............................. 604/179 |
| 4,891,846 | 1/1990 | Sager et al. . |
| 5,031,639 | 7/1991 | Wolfer . |
| 5,142,702 | 9/1992 | Piloian . |
| 5,234,420 | 8/1993 | Horton et al. . |
| 5,257,419 | 11/1993 | Alexander . |
| 5,271,745 | 12/1993 | Fentress ............................. 604/179 |
| 5,289,896 | 3/1994 | Giglio . |
| 5,336,195 | 8/1994 | Daneshver ............................. 604/179 |

*Primary Examiner*—Michael A. Brown
*Attorney, Agent, or Firm*—Young and Basile

[57] ABSTRACT

First and second straps are attached to a dialysis catheter support band to support the band and the catheter on the abdomen of a user. The first strap is attached at two opposed ends to the band and is deployable on the front of the user's abdomen, with the second strap being deployed on the user's back and connected to the band and to the first strap. Each of the first and second straps is releasibly attachable to the band and is provided with variably length adjustment. In another embodiment, a catheter support includes a strap having a first end releasibly attached to a dialysis catheter extending from a user's abdomen and a second end attached to an intermediate portion of the strap to form a loop which encircles the neck of the user.

5 Claims, 2 Drawing Sheets

HARNESS FOR ABDOMINAL CATHETER SUPPORT BAND

This application is a division of Ser. No. 08/218,670, filed Mar. 25, 1994, now U.S. Pat. No. 5,415,183.

BACKGROUND OF THE INVENTION

The present invention relates, in general, to abdominal catheter support bands.

DESCRIPTION OF THE ART

People who require kidney dialysis have recently been provided with catheter ambulatory periontenal dialysis means which enables such people to perform dialysis themselves at their home rather than traveling to a hospital or dialysis unit for more conventional dialysis. In catheter ambulatory periontenal dialysis, a catheter and tube is mounted through the abdominal wall of such individuals to provide a connection to the portable dialysis equipment.

It is necessary to firmly support the catheter and tube end adjacent the abdomen of a user when dialysis is not being performed. Such support is conventionally provided by a band which is formed of upper and lower elastic cords which are spaced apart and sized to encircle the abdomen of a user. A flexible mesh formed of criss-crossed, flexible, elastic straps or cords are interconnected between the upper and lower cords and provide support by encircling the catheter when the band is mounted about the abdomen of a user.

However, since it is necessary to form the band of elastic and flexible materials to enable it to be easily mounted on and removed from the abdomen of a user as well as to adjust to the size and position of the catheter such a band frequently shifts vertically with respect to the abdomen of a user during normal user movement. Due to gravity and such normal movements, the band frequently slips from its desired mounting position on the abdomen of a user which decreases the support function of the band as well as possibly causing discomfort to the user.

Thus, it would be desirable to provide a harness or support for a catheter ambulatory dialysis support band which firmly supports the band about the abdomen of a user without slippage or substantial movement of the band. It would also be desirable to provide such a harness which may be easily used and mounted about the upper torso of a user. It would be desirable to provide such a harness which can be detached from the band for cleaning, replacement of the band, etc. Finally, it would also be desirable to provide a catheter support which supports an ambulatory dialysis catheter on the torso of a user during bathing.

SUMMARY OF THE INVENTION

The present invention is a harness for supporting an catheter ambulatory periontenal dialysis band about the abdomen of a user.

In one embodiment, the harness comprises strap means attached to an upper cord of a catheter support band at at least two locations to be deployed on the user's front and back when mounted on the user. The strap means are deployable over the neck and shoulders of a user to support the catheter support band on the abdomen of a user to firmly retain a catheter on the user's abdomen. In one embodiment, the strap means includes a first strap having first and second ends. First means are provided for attaching the first and second ends of the strap to the upper cord of the support band in a spaced arrangement disposed on opposite sides of the catheter when the band is mounted about the abdomen of a user. The harness also includes a second strap having first and second ends. Second means are provided for attaching the first end of the second strap to the upper cord of the band and for attaching the second end of the second strap to the first strap between the first and second ends of the first strap.

In a preferred embodiment, the first and second attaching means include releasible attaching means. The releasible attaching means preferably comprises folding over the first and second ends of the first strap and the first end of the second strap and providing mating fasteners on the overlying portions of the first and second ends of the first strap and the first end of the second strap for releasibly connecting the overlaying portions of the first and second ends of the first strap and the first end of the second strap to the first strap after such ends have been wrapped around the upper cord of the support band.

Further, each of the first and second straps is preferably provided with length adjustment means for adjusting the length of each of the first and second straps to fit the size of a particular user.

In a second embodiment, a strap is provided for supporting an external dialysis catheter on the torso of a user. The strap has first and second ends, with a first attaching means mounted on the first end of the strap for releasibly attaching the first end of the strap to the catheter. The second end of the strap is connected to an intermediate portion of the strap between the first and second ends thereof to form a loop which encircles and mounts the strap about the neck of a user.

In this second embodiment, the first attaching means preferably comprises releasible attaching means provided by folding over the first end of the strap onto the strap and providing mating fasteners on the overlaying portions of the folded over first end and the adjacent portion of the strap to encircle and releasibly attach the first end of the strap to a catheter.

The second end of the strap also preferably includes releasible attaching means in the form of a releasible fastener which releasibly engages a mating fastener on an overlaying portion. Further, a plurality of fasteners may be spaced from the second end of the strap to provide adjustment in the size of the loop formed by attaching the second end of the strap to the intermediate portion of the strap.

The present invention uniquely provides a support for securing a catheter support band firmly about the abdomen of a user without movement or slippage of the band. The support or harness is easily deployed over the torso of a user and is adjustable in size to suit the particular size of a user. Further, the support or harness is releasibly attached to the catheter support band to permit separation of the support or harness of the band for replacement or cleaning of the harness and/or the support band.

BRIEF DESCRIPTION OF THE DRAWING

The various features, advantages and other uses of the present invention will become more apparent by referring to the following detailed description and drawing in which.

DESCRIPTION OF THE PREFERRED EMBODIMENTS

Figure 1:
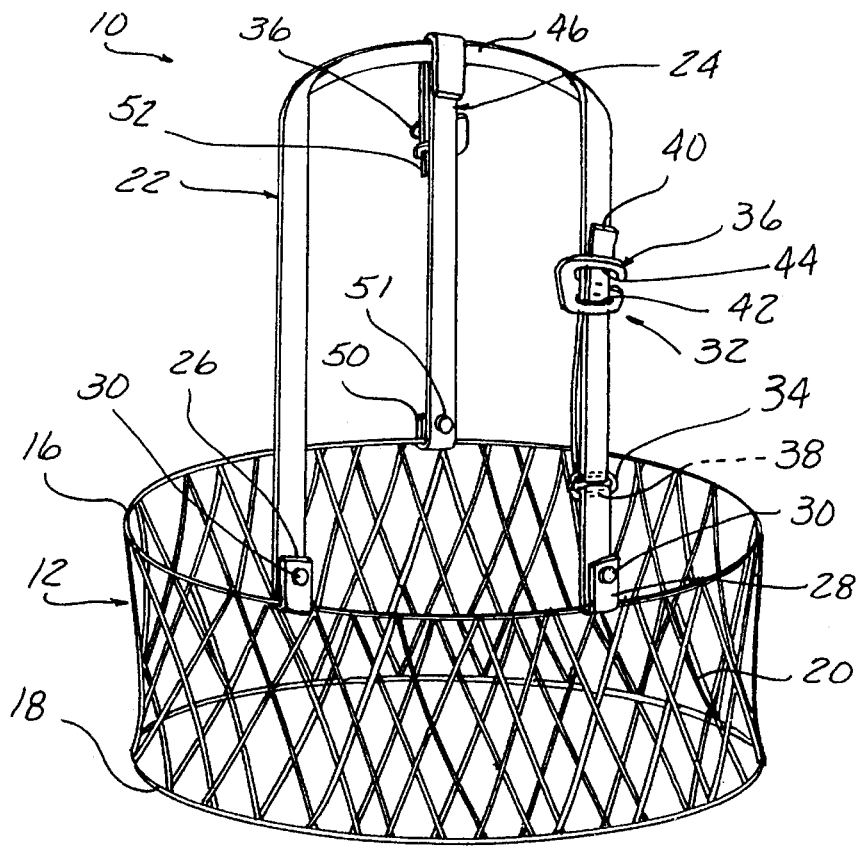
FIG. 1 is a perspective view of a first embodiment of the harness of the present invention.
Figure 2:
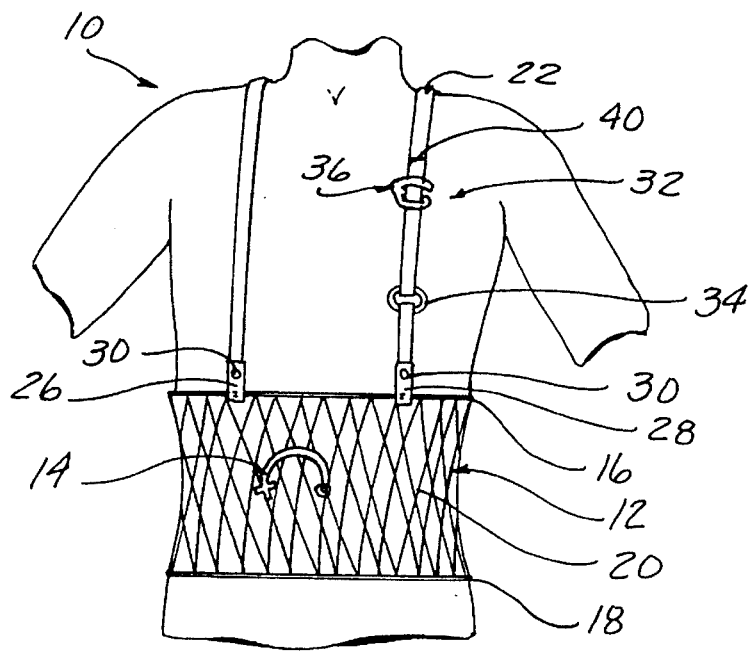
FIG. 2 is a front elevational view showing the front portion of the harness depicted in FIG. 1 mounted on the torso of a user.
Figure 3:
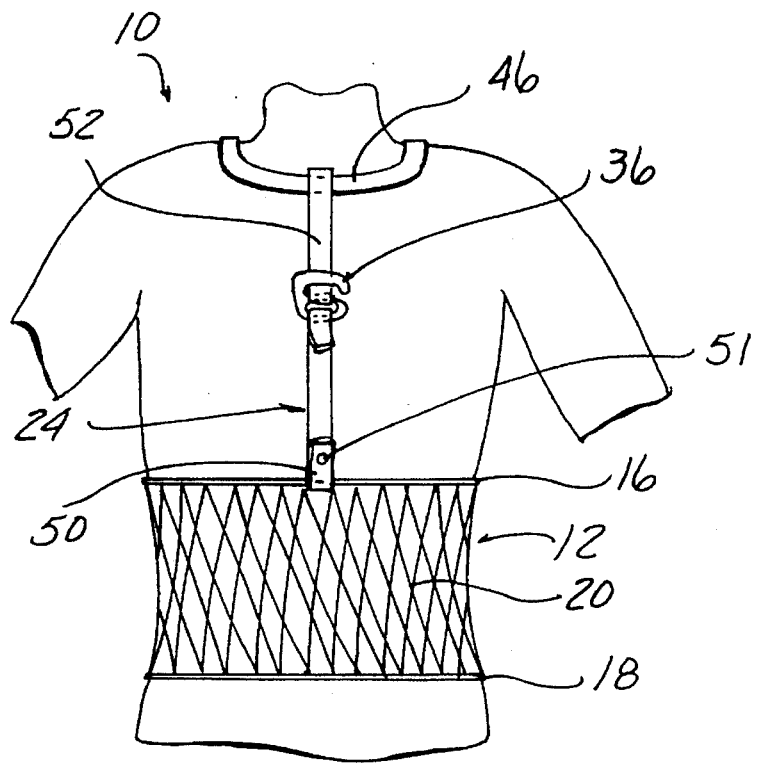
FIG. 3 is a rear elevational view of the harness depicted in FIG. 1 mounted on the torso of a user.

Referring now to the drawing, and to FIGS. 1–3 in particular, there is depicted a harness 10 which supports an ambulatory catheter support band 12 in a secure position about the abdomen of a user wherein the band 12 firmly supports an external catheter 14 extending through the abdomen of such a user.

As is conventional, the band 12 includes upper and lower spaced, elastic cords 16 and 18, respectively. The upper and lower cords 16 and 18 are each continuous and expandable to permit the band 12 to be mounted about the abdomen of a user. A plurality of criss-cross arranged straps or cords 20 are connected between the upper and lower cords 16 and 18. The straps 20 are also formed of a flexible, elastic material to permit their conformance to the size of the user's abdomen as well as to firmly surround and support the catheter 14 in a substantially fixed position on the abdomen of a user when the band 12 is mounted about the abdomen.

The harness 10 of the present invention includes strap means preferably including first and second straps 22 and 24, respectively. It will be understood that the first and second straps 22 and 24 may be deployed in any configuration about the upper torso of a user, with the configuration described hereafter being the one example.

The first strap 22 is formed of a suitable, comfortable material, such as cloth, nylon, etc.. The first strap 22 may be non-elongatable or it may be formed of a suitable, slightly elastic material.

The first strap 22 has a first end 26 and an opposed second end 28. The first and second ends 26 and 28 are attached to the upper cord 16 of the support band 12 and are generally spaced apart on the front torso or abdomen of a user as shown in FIG. 2 when the harness 10 and the support band 12 are mounted on the upper torso of the user. Although the first and second ends 26 and 28 of the first strap 22 may be permanently affixed to the upper cord 16, it is preferred that the first and second ends 26 and 28 be provided with releasibly attachable means to permit the first strap 22 to be easily connected to and detached from the upper cord 16 of the support band 12.

The releasible attaching means may take any suitable form. In one exemplary embodiment, which is meant to be exemplary only and not to limit, the attaching means to the depicted configuration, the first and second ends 26 and 28 of the first strap 22 are wrapped around the upper cord 16 and folded over onto an adjacent portion of the first strap 22 adjacent the first and second ends 26 and 28, respectively, as shown in FIGS. 1 and 2. Releasible, mating fasteners 30 are mounted on the first and second ends 26 and 28 and, also, on the overlaying portions of the first strap 22 for attachment of the first and second ends 26 and 28 to the overlaying portions of the first strap 22. The fasteners 30 preferably comprise mating snaps, although other suitable fastening means, such as mating VELCRO fasteners, may also be employed.

The first strap 22 is also preferably provided with length adjustment means denoted generally by reference number 32. The length adjustment means 32 preferably comprises a circular ring 34 and a clip 36. The first strap 22 is separated adjacent the second end 28, with one separated end 38 then firmly secured to the ring 34. The opposed separated end 40 of the first strap 22 is looped around an opposed portion of the ring 34 and slidably inserted through a pair of spaced slots 42 and 44 in the clip 36. As is conventional, the clip 36 enables the length of the first strap 22 to be adjusted with respect to the second end 28 by sliding the separated end 40 of the strap further through or out of the slots 42 and 44 in the clip 36. In this manner, the first strap 22 may be adjusted to any variably selected length to suit the particular size of a user of the harness 10 of the present invention.

Alternately, in place of the ring 34, the second end 28 of the first strap 22 can be looped around the upper cord 16 and then directly through the clip 36.

It should also be noted that in place of the ring 34 and clip 36, a certain amount of length adjustment may be provided by employing VELCRO fasteners at the first ends 26 and 28 of the first strap 22. Such fasteners, in addition to their function of releasibly attaching the first and second ends 26 and 28 of the first strap 22 to the upper cord 16 of the band 12, also may be adjusted in length of overlap to permit the overall length of the first strap 22 with respect to the upper cord 16 of the band 12 to be adjusted in length.

In use, the first and second ends 26 and 28 of the first strap 22 are wrapped around and connected to overlaying portions of the first strap 22 as shown in FIG. 1. This positions an intermediate portion 46 of the first strap 22 over the shoulders and around the neck of a user.

The second strap 24 has a first end 50 and an opposed second end 52 and is formed of the same material as the first strap 22. The first end 50 of the second strap 24 is attached to the upper cord 16 of the band 12, generally at a back portion of the band 12 when the band 12 is mounted about the abdomen of a user as shown in FIG. 3. Preferably, the attaching means is a releasibly attaching means formed, in an exemplary embodiment, by folding over the first end 50 of the second strap 24 around the upper cord 16 of the band 12 and in an overlying arrangement with an adjacent portion of the second strap 24. Mating fasteners denoted by reference number 51 are mounted on the overlaying portions of the first end 50 and the second strap 24 to releasibly attach the folded over, overlaying portions together to secure the first end 50 of the second strap 24 to the upper cord 16 of the band 12. Such fasteners 51 may be suitably formed snaps, VELCRO fasteners, etc.

The second strap 24 also includes means for attaching the second end 52 of the second strap 24 to the intermediate portion 46 of the first strap 22. Although the second end 52 of the second strap 24 may be permanently attached, such as by stitching, adhesive, etc., to the first strap 22, it is preferred that the second end 52 of the second strap 24 be releasibly attached to the intermediate portion 46 of the first strap 22. This is achieved in an exemplary embodiment by folding over the second end 52 of the second strap 24 into an overlaying arrangement with an adjacent portion of the second strap 24 as shown in FIGS. 1 and 3. Although mating fasteners, similar to fasteners 30 and 51, may be employed to secure the overlaying portions of the second strap 24 together around the intermediate portion 46 of the first strap 22, it is preferred that the second end 52 of the second strap 24 be passed through a suitable length adjusting clip 36, identical to the clip 36 employed on the first strap 22. This enables the length of the second strap 24 to be adjusted as well as connecting the second strap 24 to the first strap 22.

In use, when the harness 10 is connected to the band 12 and the harness 10 and band 12 are mounted about the abdomen of a user with the intermediate portion 46 of the first strap 22 encircling the neck of the user, the first strap 22 supports the front portion of the band 12 while the second strap 24 supports the rear portion of the band 12. The harness 10 thus prevents the band 12 from sliding up or down the abdomen of a user during normal movement of the user. This retains the band 12 in its desired position thereby firmly supporting the catheter 14 in position on the abdomen of the user.

Figure 4:
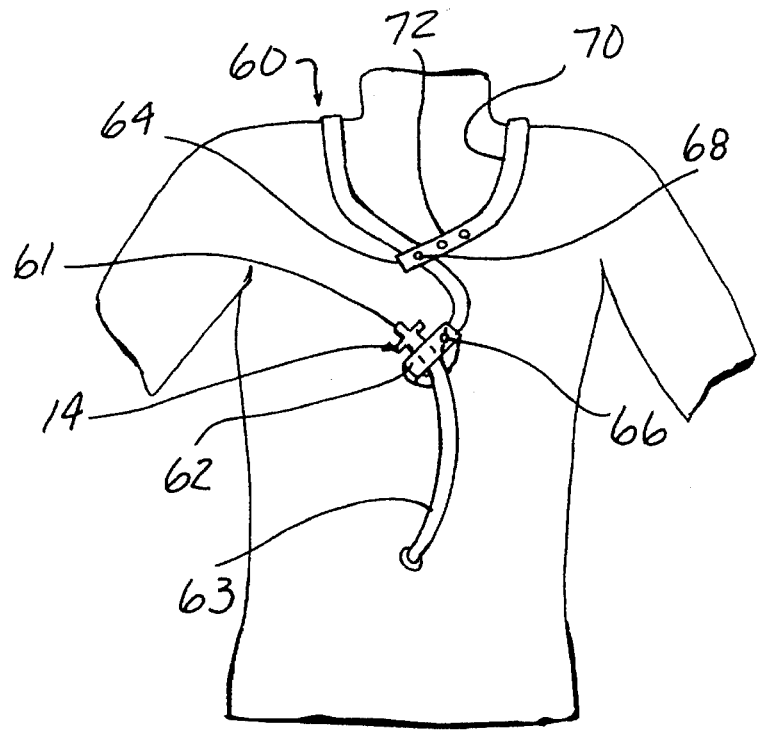
FIG. 4 is a front elevational view of a catheter support mounted on the upper torso of a user.

Another embodiment of a ambulatory periontenal dialysis catheter support is shown in FIG. 4. In this embodiment, the support 60 is designed to support a catheter 14 on the upper torso of a user during bathing or showering. The support 60 is in the form of an elongated strap having a first end 62 and an opposed second end 64. The support or strap 60 is formed of a suitable material, such as cloth, etc., which may be non-stretchable or which may be provided with a certain amount of elasticity.

Releasible attaching means are provided for releasibly attaching the first end 62 of the strap 60 to the catheter 14, preferably adjacent the connector 61 mounted on the end of a catheter tube 63. The releasible attaching means is preferably provided by folding over the first end 62 of the strap 60 in an overlaying arrangement with an adjacent portion of the strap 60. Suitable mating fasteners denoted by reference number 66 are provided on the overlaying portions of the strap 60 to secure the overlaying first end 62 to the strap 60 and around the catheter tube 63, as shown in FIG. 4. Other fasteners, such as VELCRO, may also be employed to releasibly attach the first end 62 to the overlaying portion of the strap 60.

The second end 64 of the strap 60 is attached to an intermediate portion preferably at a position spaced from the first end 62 of the strap 60. Although the second end 64 of the strap 60 may be permanently attached to the intermediate portion of the strap 60, it is preferred that the second end 60 be provided with releasible attaching means. Such releasible attaching means may be formed of mating fasteners 68, such as snaps, VELCRO, etc., which are mounted on the overlaying portions of the strap 60 to releasibly attach the second end 64 of the strap 60 to the intermediate portion of the strap 60.

When the second end 64 of the strap 60 is secured to the intermediate portion of the strap 60, a loop denoted by reference number 70 in FIG. 4 is formed which is insertable over the shoulders and around the neck of a user to mount the strap 60 on the user and to securely position the catheter 14 against the abdomen of a user during bathing, showering, etc.

The diameter of the loop 70 may be adjusted by simply providing a plurality of additional fasteners 72 spaced along the length of the strap from the second end 64 thereof. In this manner, the length of the overlaying portion of the second end 64 with respect to the adjacent portion of the strap 60 may be adjusted to vary the loop 70 to any desired size.

In summary, there has been disclosed a unique harness and support for firmly positioning a catheter support band or the catheter itself in position on the abdomen of a dialysis user. The harness and support are quickly and easily attached to the catheter support band or the catheter itself and can be easily placed over the torso of the user. The harness and support are also detachable from the support band or the catheter to permit washing of the various components, replacement, etc.

What is claimed is:

1. A support for supporting an external catheter on the torso of a user comprising:

a strap having first and second opposed ends;

first and second intermediate portions, wherein said first intermediate portion is adjacent to said first end and said second intermediate portion is spaced between said second end and said first intermediate portion;

first means, mounted on the first end of the strap, for releasibly attaching the first end of the strap to an external catheter extending from the abdomen of a user; and second means, mounted on the second opposed end of the strap, for attaching the second end of the strap to the second intermediate portion of the strap spaced from the first end of the strap to form a loop to encircle the neck of the user and to mount the strap about the neck of a user.

2. The support of claim 1 wherein the first releasibly attaching means comprises:

the first end of the strap being folded over into overlaying engagement with the first intermediate portion of the strap; and fastening means, mounted on the overlying portions of the first end and the strap, for releasibly securing the first end of the strap to the first intermediate portion of the first strap and around an exterior catheter.

3. The support of claim 1 wherein the second attaching means includes releasible attaching means for releasibly attaching the second end of the strap to the second intermediate portion of the strap.

4. The support of claim 3 wherein the releasible attaching means comprises:

fastening means, mounted on the second end of the strap and the second intermediate portion of the strap, for releasibly securing the second end of the strap to the second intermediate portion of the strap.

5. The support of claim 4 further comprising:

a plurality of spaced apart fastening means spaced from the second end of the strap to adjust the diameter of a loop formed when the second end of the strap is attached to the second intermediate portion of the strap.

* * * * *